United States Patent [19]

Bouffard

[11] Patent Number: 5,399,552
[45] Date of Patent: Mar. 21, 1995

[54] ANTIBIOTIC PEPTIDES BEARING AMINOALKYLTHIOETHER MOIETIES

[75] Inventor: Frances A. Bouffard, Scotch Plains, N.J.

[73] Assignee: Merck & Co, Inc, Rahway, N.J.

[21] Appl. No.: 775,772

[22] Filed: Oct. 17, 1991

[51] Int. Cl.$^6$ ............................................. A61K 37/02
[52] U.S. Cl. ........................................ 514/11; 530/317
[58] Field of Search .................. 530/317; 435/71.1; 514/11

[56] References Cited

U.S. PATENT DOCUMENTS

| | | | |
|---|---|---|---|
| 4,062,966 | 12/1977 | Gymer | 514/397 |
| 4,220,577 | 9/1980 | Brandman | 523/122 |
| 4,287,120 | 9/1981 | Abbot | 260/112.5 |
| 4,293,482 | 10/1981 | Abbot | 530/317 |
| 5,021,341 | 6/1991 | Giacobbe | 435/71.1 |

FOREIGN PATENT DOCUMENTS

| | | | |
|---|---|---|---|
| 851310 | 8/1977 | Belgium . | |
| 859067 | 3/1978 | Belgium . | |
| 0447186 | 3/1991 | European Pat. Off. | C07K 7/56 |
| 0459564 | 5/1991 | European Pat. Off. | C07K 7/56 |

OTHER PUBLICATIONS

Traber, R. *Helvetica Chimica Acta* 62, 1252 to 1267, 1979.

*Primary Examiner*—Robert J. Hill, Jr.
*Assistant Examiner*—David Lukton
*Attorney, Agent, or Firm*—Elliott Korsen; Mark R. Daniel; Joseph F. DiPrima

[57] ABSTRACT

Certain aminoalkyl thioethers represented by the formula

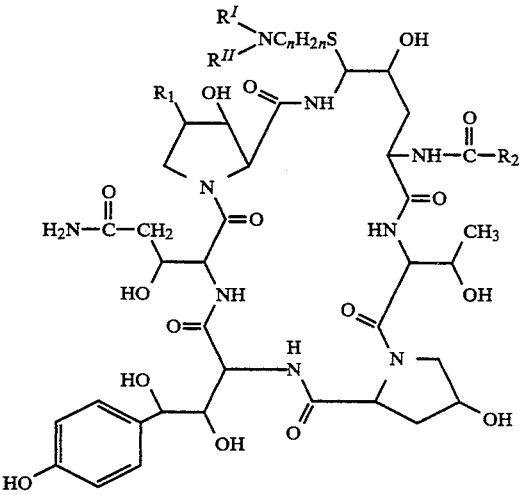

their acid addition salts and quaternary ammonium salts are described. The compounds have useful antimicrobial properties.

4 Claims, No Drawings

ANTIBIOTIC PEPTIDES BEARING AMINOALKYLTHIOETHER MOIETIES

The present invention is directed to certain aminoalkyl thioethers, Compound A (SEQ ID NOS. 1-3) which may be:

(A) an aminoalkyl thioether Compounds A-I (SEQ ID NOS. 1-3) represented by the formula:

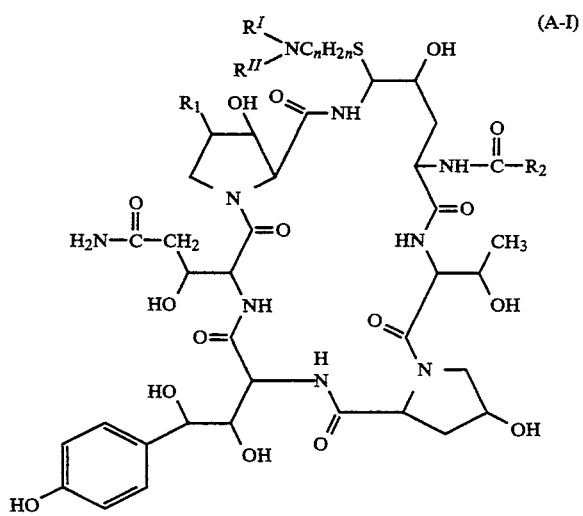

or its acid addition salt, or (B) an ammoniumalkyl thioether, Compounds A-II (SEQ ID NOS. 1-3) represented by the formula:

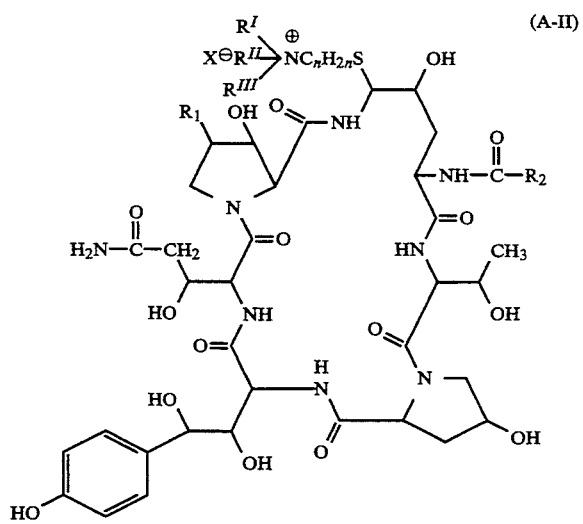

In the foregoing and succeeding formulas:

$R_1$ is H, OH or $CH_3$ $R_2$ is $C_9$–$C_{21}$ alkyl, $C_9$–$C_{21}$ alkenyl or $C_1$–$C_{10}$ alkoxyphenyl $R^I$, $R^{II}$ and $R^{III}$ are independently hydrogen, $C_1$–$C_4$ alkyl or benzyl $X^-$ is an anion of a pharmaceutically acceptable salt; and n is from 2 to 6.

Hereinafter, when the expression "aminoalkyl thioether compound" is employed, it is intended to embrace the aminoalkyl thioether of formula (A-I), its acid addition salt and ammoniumalkyl thioether of formula (A-II). "Compound A-I" will refer to the acid addition salt as well as the free base and "Compound A-II" will refer to the quaternary ammonium salt.

Where the expression "alkyl" "alkenyl" or "alkoxy" is employed, it is intended to include branched as well as straight chain radicals.

Pharmaceutically acceptable salts suitable as acid addition salts, as well as salts providing the anion of the quaternary salt, are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in Journal of Pharmaceutical Science, 66, 2 (1977).

Representative nuclei for the thioether compounds, Compound I, and the sequence ID for these compounds may be seen in the following table. Since the amino acid nuclei would be the same irrespective of substituents $R^I$, $R^{II}$ or $R^{III}$ as well as $R_2$, the sequence identification number is assigned for the nuclear variations so that the amines and ammonium salts have the same sequence ID's, as well as compounds having a different lipophilic side chain or different substituent on the nitrogen of the aminoalkyl thioether.

| Thioether Compound | $R_1$ | SEQ ID |
|---|---|---|
| A-1 | H | 1 |
| A-2 | $CH_3$ | 2 |
| A-3 | OH | 3 |

The compound which is particularly useful as an antibiotic for the control of antifungal and antipneumocystis infections may be represented by the following formula:

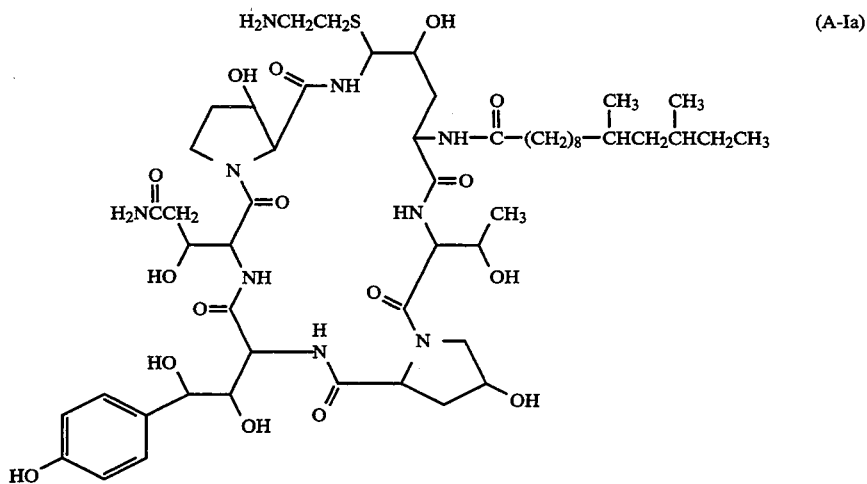

(A-Ia)

When the compounds are in a non-quaternized form they are soluble in solvents such as lower alcohols, polar aprotic solvents such as dimethyl sulfoxide (DMSO), dimethylformamide (DMF) and pyridine. They are insoluble in solvents such as ether and acetonitrile.

When the compounds are in the quaternized form, they are soluble also in water.

The compounds of the present invention are useful as an antibiotic, especially as an antifungal agent. As antifungal agents they are useful for the control of both filamentous fungi and yeasts. They are especially adaptable to be employed for the treatment of mycotic infections in mammals, especially those caused by Candida species such as *C. albicans*, *C. tropicalis*, *C. pseudotropicalis* and *C. parapsilosis*, as well as Sacchromyces species, as represented by *Sacchromyces cerevisiae*. They are also useful for the treatment and/or alleviation of *Pneumocystis carinii* pneumonia to which immune compromised patients are especially susceptible.

The compounds of the present invention which are amino or non-quaternized aminoalkyl thioethers may be prepared by the reaction of cyclohexapeptide compound (Compound E: Seq ID Nos. 4–6), an aminoalkane thiol and camphorsulfonic acid in an aprotic solvent under anhydrous conditions for time sufficient for reaction to take place with the formation of Compound A-I or A-II as the desired product as seen from the following equation:

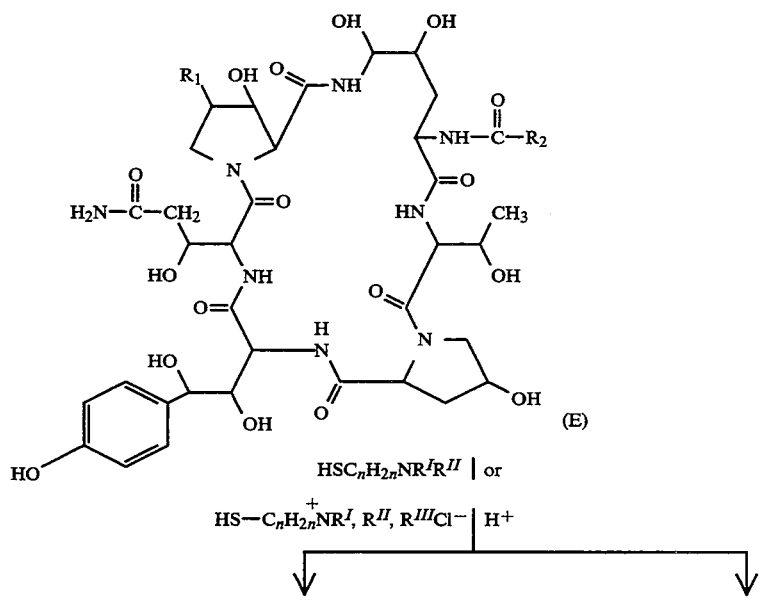

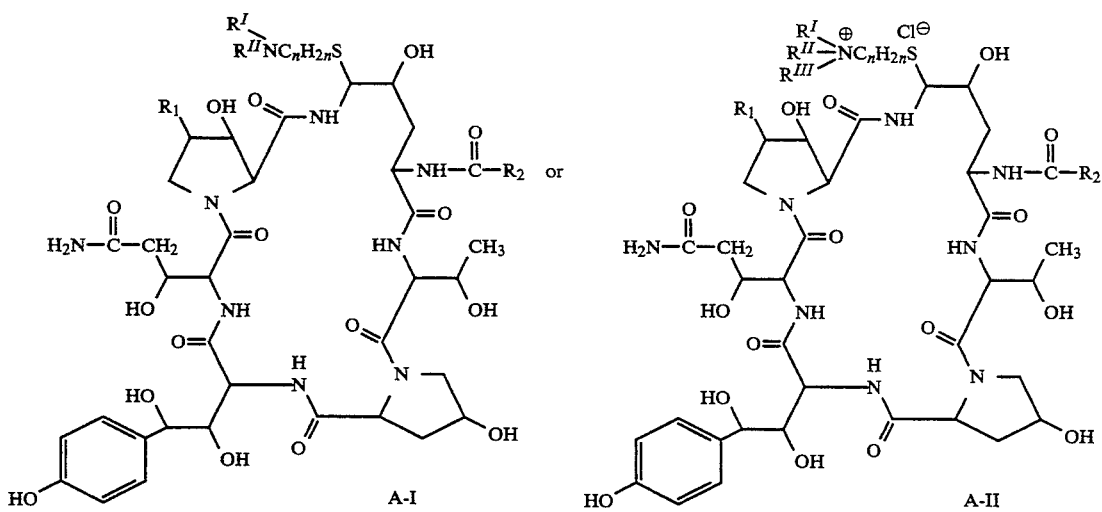

Suitable acids include a strong organic acid or a mineral acid. Examples of strong organic acids are camphorsulfonic acid, p-toluenesulfonic acid and methanesulfonic acid. Mineral acids include hydrochloric acid and hydrobromic acid. Hydrochloric acid and camphorsulfonic acids are preferred.

The sequence ID for the starting material (E) may be seen in the following table:

| Starting Material (E) | $R_1$ | SEQ. ID |
|---|---|---|
| E-1 | H | 4 |
| E-2 | $CH_3$ | 5 |
| E-3 | OH | 6 |

Suitable solvents include dimethylformamide (DMF), dimethyl sulfoxide (DMSO), 1-methyl-2-pyrrolidinone and hexamethyl phosphoric triamide (HMPA). DMF or DMSO is preferred.

The reaction is generally carried out at ambient temperature from 1 to about 10 days.

In carrying out the reaction, the cyclohexapeptide compound, the aminoalkanethiol and camphorsulfonic acid or other acid condensing agent are stirred together in a suitable solvent until the reaction is substantially complete. The reaction mixture then is diluted with water and flash chromatographed on reverse phase resins using 10 to 40 percent acetonitrile/water as eluant. The fractions containing the desired product may be concentrated and lyophilized and the lyophilized material purified by preparative HPLC.

The compounds of the present invention are active against many fungi and particularly against Candida species. The antifungal properties may be illustrated with the minimum fungicidal concentration (MFC) determination against certain Candida organisms in a microbroth dilution assay carried out in a Yeast Nitrogen Base (Difco) medium with 1% dextrose (YNBD).

In carrying out the assay, Compound A-Ia was solubilized in 10 percent dimethyl sulfoxide (DMSO) and diluted to 2560 µg/ml. The compound was then diluted to 256 µg/ml in YNBD. 0.15 mL of the suspension was dispensed to the top row of a 96-well plate (each well containing 0.15 ml of YNBD) resulting in a drug concentration of 128 µg/ml. Two-fold dilutions were then made from the top row to obtain final drug concentrations ranging from 128 to 0.06 µg/ml.

The yeast cultures, maintained on Sabouraud dextrose agar were transferred to YN broth (Difco) and incubated overnight at 35° C. with shaking (250 rpm). After incubation, each culture was diluted in sterile water to yield a final concentration of $1-5 \times 10^6$ colony forming units (CFU)/ml.

96-well microplates were inoculated using a MIC-2000 (Dynatech) which delivers 1.5 ml per well yielding a final inoculum per well of $1.5-7.5 \times 10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 µl samples from the wells in the 96-well microplate were transferred to a single well tray containing Sabouraud dextrose agar. The inoculated trays were incubated 24 hours at 28° C. and then read for minimum fungicidal concentration (MFC). MFC is defined as the lowest concentration of drug showing no growth or less than 4 colonies per spot. The results were as follows:

| Organism | | MFC µg/mL |
|---|---|---|
| C. Albicans | MY 1028 | 0.5 |
| C. Albicans | MY 1055 | 0.5 |
| C. Albicans | MY 1730 | 0.125 |
| C. tropicalis | MY 1012 | 0.125 |
| C. pseudotropicalis | MY 1100 | 0.25 |
| C. parapsilosis | MY 1010 | 0.25 |

The compounds also show in vivo effectiveness against fungi which may be demonstrated with Compound A-Ia.

Growth from an overnight SDA culture of Candida albicans MY 1055 was suspended in sterile saline and the cell concentration determined by hemacytometer count and the cell suspension adjusted to 3.75 x 105 cells/ml. Then 0.2 milliliter of this suspension was administered I.V. in the tail vein of mice so that the final inoculum was $7.5 \times 10^4$ cells/mouse.

The assay then was carried out by administering aqueous solutions of Compound A-Ia at various concentrations intraperitoneally (I.P.), twice daily (b.i.d.) for four consecutive days to 18 to 20 gram female DBA/2 mice, which previously had been infected with *Candida albicans* in the manner described above. Distilled water was administered I.P. to *C. albicans* challenged mice as controls. After seven days, the mice were sacrificed by carbon dioxide gas, paired kidneys were removed aseptically and placed in sterile polyethylene bags containing 5 milliliters of sterile saline. The kidneys were homogenized in the bags, serially diluted in sterile saline and aliquots spread on the surface of SDA plates. The plates were incubated at 35° C. for 48 hours and yeast colonies were enumerated for determination of colony forming units (CFU) per gram of kidneys. Compound A-Ia gave 99 percent reduction of recoverable Candida CFUs at 0.4 mg/kg I.P. twice daily for four consecutive days.

The compounds of the present invention may also be useful for inhibiting or alleviating *Pneumocystis carinii* infections in immune compromised patients. The efficacy of the compounds of the present invention for therapeutic or anti-infective purposes may be demonstrated in studies on immunosuppressed rats in which Sprague-Dawley rats (weighing approximately 250 grams) are immunosuppressed with dexasone in the drinking water (2.0 mg/L) and maintained on a low protein diet for seven weeks to induce the development of pneumocystis pneumonia from a latent infection. Before drug treatment, two rats are sacrificed to confirm the presence of *Pneumocystis carinii* pneumonia (PCP). Five rats (weighing approximately 150 grams) are injected twice daily for four days subcutaneously (sc) with Compound A-Ia in 0.25 ml of vehicle (distilled water). A vehicle control is also carried out. All animals continue to receive dexasone in the drinking water and low protein diet during the treatment period. At the completion of the treatment, all animals are sacrificed, the lungs are removed and processed, and the extent of disease determined by microscopic examination of stained slides for the presence of cysts. The prevention of or reduction of cysts are observed in slides from the lungs of treated rats when compared with the number of cysts in lungs of untreated controls or solvent controls.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1 percent by weight of Compound X or one of the components. Concentrate compositions suitable for dilutions prior to use may contain 90 percent or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound X with the components suitable for the medium desired.

Compositions formulated for oral administration may be a liquid composition or a solid composition. For liquid preparations, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with a lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and for injection take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. These compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use any method of administration may be employed. For treating mycotic infections, oral administration is frequently preferred.

When the compound is to be employed for control of pneumocystis infections it is desirable to directly treat lung and bronchi. For this reason inhalation methods are preferred. For administration by inhalation, the compounds of the present invention are conveniently delivered in the form of an aerosol spray presentation from pressurized packs or nebulisers. The preferred delivery system for inhalation is a metered dose inhalation (MDI) aerosol, which may be formulated as a suspension or solution of Compound A-I or A-II in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

EXAMPLE I

1-[4-hydroxy-5-aminoethylthio-$N^2$-(10,12-dimethyl-1-oxotetradecyl)ornithine]-5-(3-hydroxyglutamine)-6-(3-hydroxyproline)echinocandin B trifluoroacetate (Seq. ID No. 1)

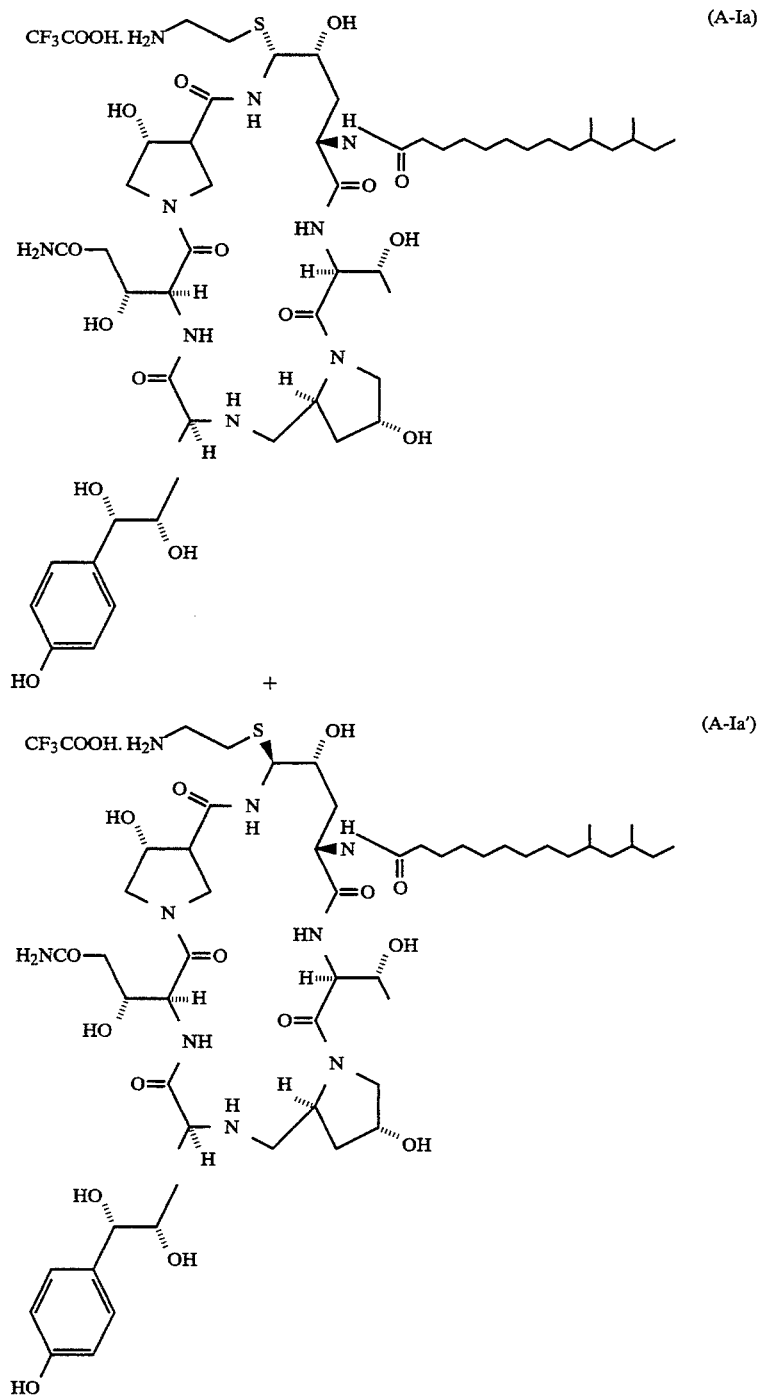

(A-Ia)

(A-Ia')

A solution of 500 milligrams (0.47 millimole) of 1-[4,5-dihydroxy-$N^2$-(10,12-dimethyl-1-oxotetradecyl)ornithine]-5-(3-hydroxy-glutamine)-6-(3-hydroxy-proline)echinocandin B, 5.34 grams (47 millimoles) of 2-aminoethanethiol hydrochloride and 109 milligrams (0.47 millimole) of (1S)-(+)-10-camphorsulfonic acid in 40 milliliters of anhydrous N,N-dimethylformamide was stirred at 25° C. for a period of 6 days. The reaction mixture was diluted with 40 milliliters of water and flash chromatographed on "LICHROPREP" (E. Merck) RP 18 (40–63 μm, 15.0 grams) packed in 10 percent acetonitrile/water. The column was eluted with 10 to 40 percent acetonitrile/water, collecting two 120 milliliter fractions at each 10 percent gradient. The second 30 percent acetonitrile/water fraction was concentrated and lyophilized to obtain 100 milligrams of material. The material was purified by preparative HPLC "ZORBAX" C8 21.2×250 mm, 35–40% $CH_3CN/H_2O$ (0.1% $CF_3COOH$) at 10 mL/min to obtain 64 milligrams (12 percent) of 1-[4-hydroxy-5-aminoethylthio-$N^2$-(10,12-dimethyl-1-oxotetradecyl)ornithine]-5-(3-hydroxy-glutamine)-6-(3-hydroxy-proline) echinocandin B trifluoroacetate (A-Ia) as a white amorphous solid: $^1H$ NMR (400 MHz, $CD_3OD$) δ1.14 (d, 3, J=6.2 Hz,$CH_3$-threo), 2.83 (m, 2, SCH₂CH₂NH₃+CF₃COO⁻), 5.44 (d,1,J=1.8 Hz, H5 orn); FAB-MS (Li), m/e 1131 (M+H+Li)+.

From the two 40 percent acetonitrile/water fractions was obtained 185 milligrams of material which was purified by preparative HPLC using a column as above described and eluting with 40 to 45 percent acetonitrile/water (0.1 percent trifluoroacetic acid) to obtain 1-[4-hydroxy-5-(epi)-aminoethylthio-N²-(10,12-dimethyl-1-oxotetradecyl)ornithine]-5-(3-hydroxy-glutamine)-6-(3-hydroxy-proline)echinocandin B trifluoroacetate (A-Ia) (128 mg, 24%) as a white amorphous solid: ¹H NMR (400 MHz, CD₃OD) δ1.34 (d, 3, J=6.3 Hz, CH₃-threo), 2.89 (m, 2, SCH₂CH₂NH₃+CF₃COO⁻), 4.72 (d, 1, J=4.9 Hz, H5 orn); FAB-MS (Li), m/e 1131 (M+H+Li)+.

EXAMPLE II

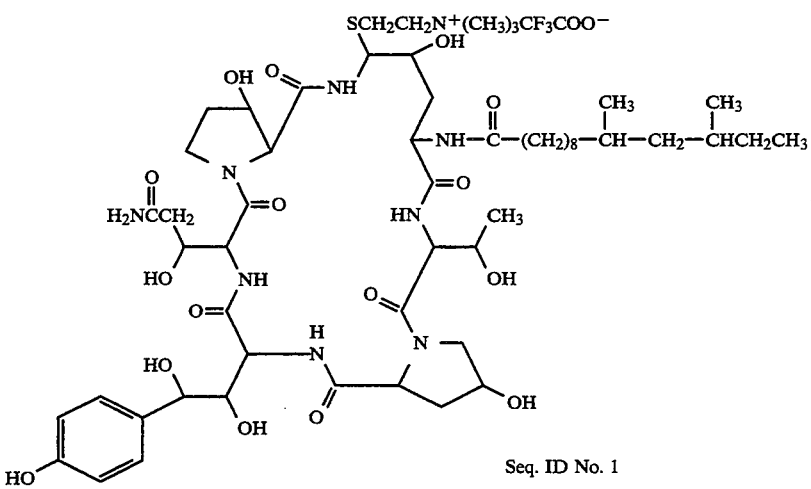

Seq. ID No. 1

To a solution of 500 milligrams of Compound A-Ia (Seq. ID No. 1) (prepared as described in Example I) and 100 equivalents of trimethylammonium ethanethiol chloride is added 109 milligrams (1 eq) of camphorsulfonic acid and the resulting mixture stirred at room temperature until HPLC analysis indicates conversion of the starting material. The reaction mixture is then injected directly onto a "ZORBAX" (21.2 mm×25 cm) C8 column and eluted with 40/60 acetonitrile/water (0.1% CF₃COOH) at 10 mL/min. Pure fractions as determined by HPLC are pooled and lyophilized to the desired product Compound A-IIa (Seq ID No. i), M.W. 1279.5, as the trifluoroacetate salt.

EXAMPLE III

In operations carried out as described in Example I and II, the following compounds in which R₁ is CH₃, and the other substituents are as set forth below (wherein if R^III is other than H, X⁻ is CF₃COO⁻) are prepared:

| Compound | R₂ | R^I | R^II | R^III | SEQ ID |
|---|---|---|---|---|---|
| III-A | DMTD* | CH₃ | CH₃ | — | 2 |
| III-B | linoleyl | CH₃ | CH₃ | — | 2 |
| III-C | linoleyl | CH₃ | CH₃ | CH₃ | 2 |
| III-D | —C₆H₄OC₈H₁₇ | CH₂C₆H₅ | CH₃ | — | 2 |
| III-E | —C₆H₄OC₈H₁₇ | CH₃ | CH₃ | CH₃ | 2 |

*DMTD = 9,11 dimethyltridecyl

EXAMPLE IV

In operations carried out as described in Example I and II, the following compounds in which R₁ is OH, and the other substituents are as set forth below (wherein if R^III is other than H, X⁻ is CF₃COO⁻) are prepared:

| Compound | R₂ | R^I | R^II | R^III | SEQ ID |
|---|---|---|---|---|---|
| IV-A | DMTD | CH₃ | CH₃ | — | 3 |
| IV-B | linoleyl | CH₃ | CH₃ | — | 3 |
| IV-C | linoleyl | CH₃ | CH₃ | CH₃ | 3 |
| IV-D | —C₆H₄OC₈H₁₇ | CH₂C₅ | CH₃ | — | 3 |
| IV-E | —C₆H₄OC₈H₁₇ | CH₃ | CH₃ | CH₃ | 3 |

EXAMPLE V 1000 compressed tablets each containing 500 mg of Compound A-Ia are prepared from the following formulation:

| Compound | Grams |
|---|---|
| Compound A-Ia | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE VI 1000 hard gelatin capsules, each containing 500 mg of Compound A-IIa are prepared from the following formulation:

| Compound | Grams |
|---|---|
| Compound A-IIa | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE VII

An aerosol composition may be prepared having the following formulation:

|  | Per Canister |
|---|---|
| Compound of Example III-D | 24 mg |
| Lecithin NF Liquid Concentrated | 1.2 mg |
| Trichlorofluoromethane, NF | 4.026 g |
| Dichlorodifluoromethane, NF | 12.15 g |

EXAMPLE VIII 250 milliliters of an injectible solution may be prepared by conventional procedures having the following formulation:

| Dextrose | 12.5 g |
|---|---|
| Water | 250 ml |
| Compound of Example IV-A | |

The ingredients are blended and thereafter sterilized for use.

Preparation of Starting Materials:

The starting materials for the compounds are natural products or derivatives of natural products.

The following compounds are natural products produced by cultivating an appropriate organism in nutrient medium as hereinafter described.

E-1 may be produced by cultivating *Zalerion arboricola* ATCC 20868 in a nutrient medium enriched in mannitol as the primary source of carbon as described in U.S. Pat. No. 5,021,341, Jun. 4, 1991.

E-2 may be produced by cultivating *Zalerion arboricola* ATCC 20868 in nutrient medium as described in U.S. Pat. No. 4,931,352, Jun. 5, 1990 or in nutrient medium enriched in glycerol as described in U.S. Pat. No. 4,968,608, Nov. 6, 1990.

E-2 nucleus with a different $R_2$ may be produced by cultivating *Acrophialophora limonispora* in nutrient medium as described in U.S. Pat. No. 4,173,629.

Starting materials in which $R_2$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as also described in Experentia 34, 1670 (1978) or U.S. Pat. No. 4,293,482, and thereafter recovering the deacylated cyclopeptide, and acylating the deacylated cyclopeptide by mixing together with an appropriate active ester $R_2COX$ to obtain Compound E with the desired acyl group as also described in U.S. Pat. No. 4,287,120;

E-3 may be produced by cultivating *Zalerion arboricola* ATCC 74030 in a nutrient medium containing assimilable sources of carbon, nitrogen and inorganic salts under aerobic conditions, and particularly with ammonium salts as immediate source of nitrogen, monobasic potassium phosphate for pH control and enriched in mannitol as primary source of carbon.

---

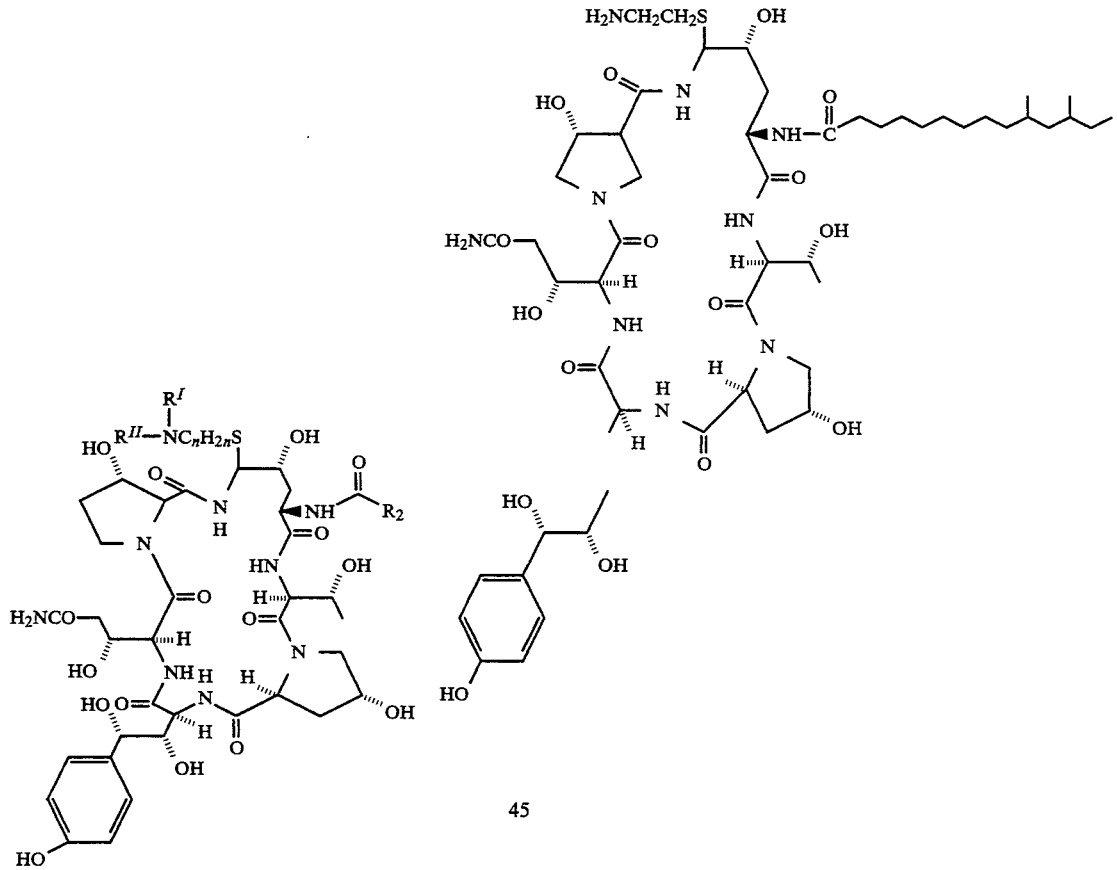

What is claimed is:

1. An aminoalkylthioether represented by the following formula:

or its acid addition salt, wherein
R$_2$ is C$_9$–C$_{21}$ alkyl or C$_9$–C$_{21}$ alkenyl,
R$^I$ and R$^{II}$ are independently hydrogen, C$_1$–C$_4$ alkyl or benzyl;
n represents an integer from 2 to 6.

2. An antibiotic pharmaceutical composition comprising a pharmaceutically effective amount of a compound of claim 1 in a pharmaceutically acceptable carrier.

3. A composition according to claim 2 in unit dosage form wherein the compound is present in an amount ranging from 10 milligrams to 200 milligrams.

4. A compound having the structural formula:

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 1:

Xaa  Thr  Xaa  Xaa  Xaa  Xaa
        1                          5

( 2 ) INFORMATION FOR SEQ ID NO: 2:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 2:

Xaa  Thr  Xaa  Xaa  Xaa  Xaa
        1                          5

(2) INFORMATION FOR SEQ ID NO: 3:

(i) SEQUENCE CHARACTERISTICS:
    (A) LENGTH: 6
    (B) TYPE: AMINO ACID
    (C) STRANDEDNESS: NA
    (D) TOPOLOGY: CIRCULAR (ii) MOLECULE TYPE:
    (A) DESCRIPTION: PEPTIDE (xi) SEQUENCE DESCRIPTION: SEQ ID NO: 3:

Xaa Thr Xaa Xaa Xaa Xaa
    1           5

(2) INFORMATION FOR SEQ ID NO: 4:

(i) SEQUENCE CHARACTERISTICS:
    (A) LENGTH: 6
    (B) TYPE: AMINO ACID
    (C) STRANDEDNESS: NA
    (D) TOPOLOGY: CIRCULAR (ii) MOLECULE TYPE:
    (A) DESCRIPTION: PEPTIDE (xi) SEQUENCE DESCRIPTION: SEQ ID NO: 4:

Xaa Thr Xaa Xaa Xaa Xaa
    1           5

(2) INFORMATION FOR SEQ ID NO: 5:

(i) SEQUENCE CHARACTERISTICS:
    (A) LENGTH: 6
    (B) TYPE: AMINO ACID
    (C) STRANDEDNESS: NA
    (D) TOPOLOGY: CIRCULAR (ii) MOLECULE TYPE:
    (A) DESCRIPTION: PEPTIDE (xi) SEQUENCE DESCRIPTION: SEQ ID NO: 5:

Xaa Thr Xaa Xaa Xaa Xaa
    1           5

(2) INFORMATION FOR SEQ ID NO: 6:

(i) SEQUENCE CHARACTERISTICS:
    (A) LENGTH: 6
    (B) TYPE: AMINO ACID
    (C) STRANDEDNESS: NA
    (D) TOPOLOGY: CIRCULAR (ii) MOLECULE TYPE:
    (A) DESCRIPTION: PEPTIDE (xi) SEQUENCE DESCRIPTION: SEQ ID NO: 6:

Xaa Thr Xaa Xaa Xaa Xaa
    1           5